(12) United States Patent
Muessig et al.

(10) Patent No.: US 9,905,916 B2
(45) Date of Patent: Feb. 27, 2018

(54) ANTENNA AND IMPLANTABLE MEDICAL DEVICE

(71) Applicant: BIOTRONIK SE & Co. KG, Berlin (DE)

(72) Inventors: Dirk Muessig, West Linn, OR (US); Jeffrey A. von Arx, Lake Oswego, OR (US); Eric Austin, Portland, OR (US); James E. Brown, Tigard, OR (US)

(73) Assignee: Biotronik SE & Co. KG, Berlin (DE)

( * ) Notice: Subject to any disclaimer, the term of this patent is extended or adjusted under 35 U.S.C. 154(b) by 108 days.

(21) Appl. No.: 14/943,715

(22) Filed: Nov. 17, 2015

(65) Prior Publication Data

US 2016/0164170 A1 Jun. 9, 2016

Related U.S. Application Data

(60) Provisional application No. 62/087,817, filed on Dec. 5, 2014.

(51) Int. Cl.
| | |
|---|---|
| *H01Q 1/22* | (2006.01) |
| *H01Q 1/36* | (2006.01) |
| *A61N 1/372* | (2006.01) |
| *H01Q 1/27* | (2006.01) |
| *H01Q 9/42* | (2006.01) |
| *A61N 1/375* | (2006.01) |

(52) U.S. Cl.
CPC .......... *H01Q 1/362* (2013.01); *A61N 1/37229* (2013.01); *H01Q 1/22* (2013.01); *H01Q 1/273* (2013.01); *H01Q 1/36* (2013.01); *H01Q 9/42* (2013.01); *A61N 1/375* (2013.01); *H04R 2225/51* (2013.01)

(58) Field of Classification Search
CPC ............ H01Q 1/362; H01Q 1/22; H01Q 1/36; H01Q 9/42
USPC .......................................................... 343/718
See application file for complete search history.

(56) References Cited

U.S. PATENT DOCUMENTS

| 7,317,946 B2 | 1/2008 | Twetan et al. |
| 7,554,493 B1 | 6/2009 | Rahman |
| 2009/0228074 A1* | 9/2009 | Edgell ................ A61N 1/37229 607/60 |
| 2009/0248112 A1 | 10/2009 | Mumbru et al. |

(Continued)

OTHER PUBLICATIONS

A. Kiourti et al., "Dual-Band Implantable Antennas for Medical Telemetry: A Fast Design Methodology and Validation for Intra-Cranial Pressure Monitoring," Journal of Progress in Electromagnetics Research (JPIER), vol. 141, pp. 161-183, 2013.

(Continued)

*Primary Examiner* — Andrea Lindgren Baltzell
(74) *Attorney, Agent, or Firm* — Buchanan Ingersoll & Rooney PC

(57) ABSTRACT

An antenna for an implantable medical device with a broadened bandwidth including at least two strut-like first conducting members, wherein each adjacent pair of first conducting members is connected by a second conducting member, wherein the second conducting member has the basic form of an at least partial round and/or polygonal plate, or of at least a part of a sphere and/or polyhedron, or a cross (or X), or a star, wherein the second conducting member further includes at least one through going opening, wherein the basic form fully encircles the opening.

13 Claims, 4 Drawing Sheets

(56) References Cited

U.S. PATENT DOCUMENTS

| | | |
|---|---|---|
| 2011/0134013 A1 | 6/2011 | Rawat et al. |
| 2012/0001812 A1 | 1/2012 | Zhao et al. |
| 2012/0026066 A1* | 2/2012 | Leisten .................. H01Q 1/38 343/895 |

OTHER PUBLICATIONS

G. Clementi et al., "A Novel Low Profile Tapered Slot Antenna With Absorbing Material for Radar Imaging System", 7th European Conference on Antennas and Propagation (EuCAP), pp. 2891-2895, 2013.
B. Ooi et al., "Novel Design of Broad-Band Stacked Patch Antenna", IEEE Transactions on Antennas and Propagation, vol. 50, No. 10, pp. 1391-1395, Oct. 2002.
European Search Report and Annex to the European Search Report on European Patent Application No. EP 15 19 3419, dated Apr. 26, 2016 (11 pages).

\* cited by examiner

ANTENNA AND IMPLANTABLE MEDICAL DEVICE

CROSS-REFERENCE TO RELATED APPLICATIONS

This patent application claims the benefit of U.S. Provisional Patent Application No. 62/087,817, filed on Dec. 5, 2014, which is hereby incorporated by reference in its entirety.

TECHNICAL FIELD

Embodiments of the present invention generally refer to an antenna for an implantable medical device and a respective device.

BACKGROUND

Implantable medical devices for providing electrical stimulation to body tissues, for monitoring physiologic conditions and for providing alternative treatments to drugs, are well-known in the art. Exemplary implantable medical devices include, for example, implantable cardio defibrillators, pacemakers, and programmable neurostimulator pulse generators. The medical devices typically incorporate a power source connected with an electronic circuit having a circuit board in a hermetically sealed housing. Connected to the sealed housing often a header assembly is provided which includes electrical contact elements that are electrically coupled with the electronic circuit and/or to the power source located inside the housing via a feedthrough component. The header assembly provides a connector for electrical communication via an external medical lead cable.

Wireless communication with such implantable medical devices has become increasingly more important. Communication is necessary, for example, to program such a device, to monitor its various functions and to provide data concerning a patient's response to the devices therapy. Therefore, radio frequency (RF) transmissions are commonly employed to communicate with an implantable medical device. Therefore, such device often provides an RF telemetry antenna for transmitting or receiving signals.

U.S. Pat. No. 7,317,946 shows and describes an implantable medical device with an elongated antenna within the header for far field telemetry to ensure telemetry over distances of a few to many meters from an implantable medical device. The antenna is disposed outside the hermetically sealed housing within the header and has a serpentine arrangement, as one factor to consider for far field telemetry is the length of the antenna. In contrast, the dimensions of a medical device have to be as small as possible. However, the disclosed serpentine antenna provides a resonant length which is only valid for one narrow case. The variable nature of the actual implant conditions means that this narrow bandwidth element is at a disadvantage when operating over the entire set of possible implant environments.

U.S. Pat. No. 7,554,493 refers to a folded monopole antenna for an implantable medical device which is in particular used as RF telemetry antenna. The folded monopole antenna is electrically coupled to a metal pad located on an internal circuit board. This metal pad is coupled to a transceiver circuit for receiving and transmitting signals. Further, a circuit ground is provided which is coupled to a second metal pad and which is further coupled to a metal housing portion. The metal portion acts as antenna ground plane which effectively lengthens the antenna by lengthening the current path. The antenna is constructed of a wire or thin conductive strip that is conformable inside a biocompatible, dielectric portion of the housing. The shape of the folded antenna inside the epoxy portion includes two arcs, which arcs are connected together on one end of each arc. The antenna is thereby folded in a manner to provide the longest antenna length and maximum possible separation between the antenna and the metal portion of the housing in order to minimize interference. The folded monopole antenna described in this document is designed in such a way as to give a resonance at one particular frequency, but it is narrow in bandwidth, and thus also less appropriate for operation over the wide range of implant environments.

Higher bandwidth antennas are desirable for use in medical device telemetry because this allows for more efficient operation of the antenna over the variety of implant conditions (depth of implanted device, orientation and location of device, etc.), patient anatomies (e.g., the fat content of the tissue surrounding the implanted device can vary with age/over device lifetime, gender, etc.), and general patient-related variability (exact electromagnetic properties of the surrounding tissue). For example the dielectric constant of biological materials can vary by a factor of 10 (for example, at 403.5 MHz, the dielectric constant of fat is 5.6, while for muscle it is 57.1). This variability leads to a significant impact on the antenna performance.

In order to improve bandwidth for a telemetry antenna in an implantable medical device the article "Dual-Band Implantable Antennas For Medical Telemetry: A Fast Design Methodology And Validation For Intra-Cranial Pressure Monitoring" by A. Kiourti et al., Progress In Electromagnetics Research, Vol. 141, pages 161-183, 2013 proposes to provide one portion of the antenna that is resonant at some frequency and a second portion providing a second resonance which is slightly different but nearby.

With the same goal the document "Novel Design of Broad-Band Stacked Patch Antenna" by B. Ooi et al., IEEE Transactions on Antennas and Propagation, Vol. 50, No. 10, October 2002 suggests an E-shaped patch, also in combination with a stacked square patch.

G. Clementi et al. proposes, in the article "A Novel Low Profile Tapered Slot Antenna With Absorbing Material For Radar Imaging System", 7th European Conference on Antennas and Propagation (EuCAP), 2013, a double exponentially tapered slot antenna for microwave imaging applications. To extend the antenna's impedance bandwidth toward low frequency, an absorbing material which is stacked on the antenna sides is provided.

For implantable medical devices it is not applicable to introduce additional layers as proposed by B. Ooi et al. above due to space limitations. The same applies for introducing a second resonance with the same element as in the method described in the article of A. Kiourti et al. above. To add some resistive/lossy material, as suggested by G. Clementi et al. above, where some of the energy is dissipated, the resonant behavior is reduced (at the expense of efficiency), which is undesirable because the extra power is burned in the lossy material and some of the energy is dissipated as heat. In addition, the used materials do not seem suitable for usage in a medical device header, for biocompatible reasons.

The present invention is directed toward overcoming one or more of the above-mentioned problems.

SUMMARY

Considering the above, one or more embodiments of the present invention provide an antenna with improved bandwidth which is better feasible for an implantable medical device. Accordingly, one or more embodiments of the present invention provide a respective implantable medical device.

At least one embodiment of the present invention comprises at least two strut-like first electrically conducting members, wherein each adjacent pair of first conducting members is connected by a second electrically conducting member, wherein the second conducting member has the basic form of an at least partial round and/or polygonal plate, or of at least a part of a sphere and/or polyhedron, or a cross (or X), or a star. The second conducting member is electrically contacted by the two first conducting members in two different places.

According to at least one embodiment, the basic form of the second conducting member is selected from the group of a full circle, a full sphere or ellipsoid segment, a full polyhedron and a full polygon.

In at least one embodiment, the second conducting member further comprises at least one through going opening, wherein the basic form fully encircles the opening. Additionally, in one or more embodiments, the at least one through going opening has a round or polygonal cross section. In one or more embodiments, the form of the second conducting member is selected from the group of a full circular ring, a full squared frame, a full rectangular frame, a full triangular frame and another full polygonal frame. In one or more embodiments, if the second conducting member is of three dimensional shape, this shape may have a through going opening. Alternatively, it may be solid, or hollow, or hollowed out.

It shall be emphasized that the above mentioned form is the form of the electrically conductive material forming the antenna which may be stamped, etched or cut from a metal sheet. In one or more embodiments, the electrically conductive material forming the antenna is laser cut from a metal sheet.

In at least one embodiment, the outer diameter of the basic form of the second conducting member may be between 1 mm and 3 mm, the diameter of the at least one through going opening is between 0.5 mm and 1 mm, the width of the first conducting member is between 0.5 mm and 1 mm, the length of the first conducting member is between 1 mm and 10 mm, the thickness of the electrically conducting layer forming the first conductive member and the second conducting member is between 0.05 mm and 0.2 mm.

In at least one embodiment, the antenna comprises at least between 5 and 20 first conducting members and, accordingly, between 4 and 21 second conducting members.

In at least one embodiment, the conducting layer forming the first conducting member and the second conducting member contains at least one of the following group of materials containing Titanium grade 1 thru 4, stainless steel, gold and any other biocompatible metal material. In one or more embodiments, the conducting layer forming the first conducting member and the second conducting member contains Titanium grade 4.

The connecting second conducting member in the above mentioned form has the effect of lessening the strength of the resonant behavior (quality factor, Q) of the antenna. As the bandwidth of the antenna is inversely proportional to Q, the proposed antenna has a greater bandwidth because of the second conducting member.

Further advantages of the antenna designs are that the antenna during header assembling can be better automatically grabbed (for example, by a robot), better positioned on the header core, and better kept in place during casting the header. Hence, the production process of the header and, therefore, of the implantable medical device is simplified and made more secure so that the costs for the header production are reduced.

In at least one embodiment, the angle enclosed by an adjacent pair of first conducting members or their respective longitudinal axis is greater than or equal to 0° and not greater than 180°. In one or more embodiments the angle enclosed by an adjacent pair of first conducting members or their respective longitudinal axis is between 70° and 150°.

In at least one embodiment, each of the at least two first conducting members and the second conducting member, or both, comprise an elongated slot. In one or more embodiments, the elongated slot is through going. Further, the slot is fully encircled by the antenna metal of the first conductive member or the second conductive member, respectively. The slot may have a width between 0.2 mm and 0.4 mm and a length between 1 mm and 3 mm. The slot ensures that the electrical length of the antenna is not shorted by electrons taking the short path around the second conducting member. The slots are arranged such that the likelihood is increased that electrons take the long path around the second conducting member. This increases the electrical length of the antenna without the antenna taking up any additional space.

In at least one embodiment, the first conducting member has the form of a rod or a helix.

In one of the at least one embodiments of the present invention, the at least two first conducting members and the intermediate second conducting member are accommodated in the same planes. This means, that the first and second conduction members are in one plane, for example, in one or more embodiments, parallel to a wall or a side of the header of an implantable medical device. In another one of the at least one embodiments, the at least two first conducting members and the intermediate second conducting member are accommodated in different planes. This means that the plane forming the second conducting member is tilted with regard to the plane forming the first conducting members, wherein the tilt solid angle is between 0° and less than 360°. In case the tilt angle is 0°, the first conducting member is in the same plane as the second conducting member. In case the tilt angle is different from 0° the antenna has a non-planar geometry. The plane of the first or second conducting member is the plane in which the respective member has the biggest dimension.

In a three dimensional configuration, a first section of at least one embodiment of the antenna comprising at least one second conducting member and a pair of first conducting members is accommodated in a first plane, and a second section of the antenna comprising at least one second conducting member and a pair of first conducting members is accommodated in a second plane different from the first plane. In one or more embodiments, the first section of at least one embodiment of the antenna comprising at least one second conducting member and a pair of first conducting members is accommodated in a first plane, and a second section of the antenna comprising at least one second conducting member and a pair of first conducting members is accommodated in a second plane parallel to the first plane. Further the first section of the antenna is connected to the second section of the antenna by an electrically conducting element, preferably by a first conducting member.

A further enhancement of bandwidth is achieved if, in at least one embodiment, the antenna comprises a first section with a first resonant frequency, and at least one second section with a second resonant frequency. Therein, the second resonance is slightly different but nearby. The difference in the resonance depends on how wide the bandwidths of the first and second sections are, and the desired bandwidth to be covered by the antenna. Further, the first section of the antenna is connected to the second section of the antenna by an electrically conducting element, preferably by a first conducting member.

One or more embodiments of the present invention include an implantable medical device comprising an antenna as described above with the same advantages. In at least one embodiment, the antenna is accommodated within the header of the device.

A full and enabling disclosure of the present disclosure, including the best mode thereof, directed to one of ordinary skill in the art is set forth in the following specification of different embodiments. Thereby, further features and advantages are presented that are part of the present disclosure independently of the features specified in the dependent claims.

Further embodiments, features, aspects, objects, advantages, and possible applications of the present invention could be learned from the following description, in combination with the Figures, and the appended claims.

DETAILED DESCRIPTION

One or more embodiments of the present invention provide an antenna with improved bandwidth which is better feasible for an implantable medical device. Accordingly, a goal consists in providing a respective implantable medical device.

At least one embodiment of the present invention comprises at least two strut-like first electrically conducting members, wherein each adjacent pair of first conducting members is connected by a second electrically conducting member, wherein the second conducting member has the basic form of an at least partial round and/or polygonal plate, or of at least a part of a sphere and/or polyhedron, or a cross (or X), or a star. The second conducting member is electrically contacted by the two first conducting members in two different places.

Figure 1:
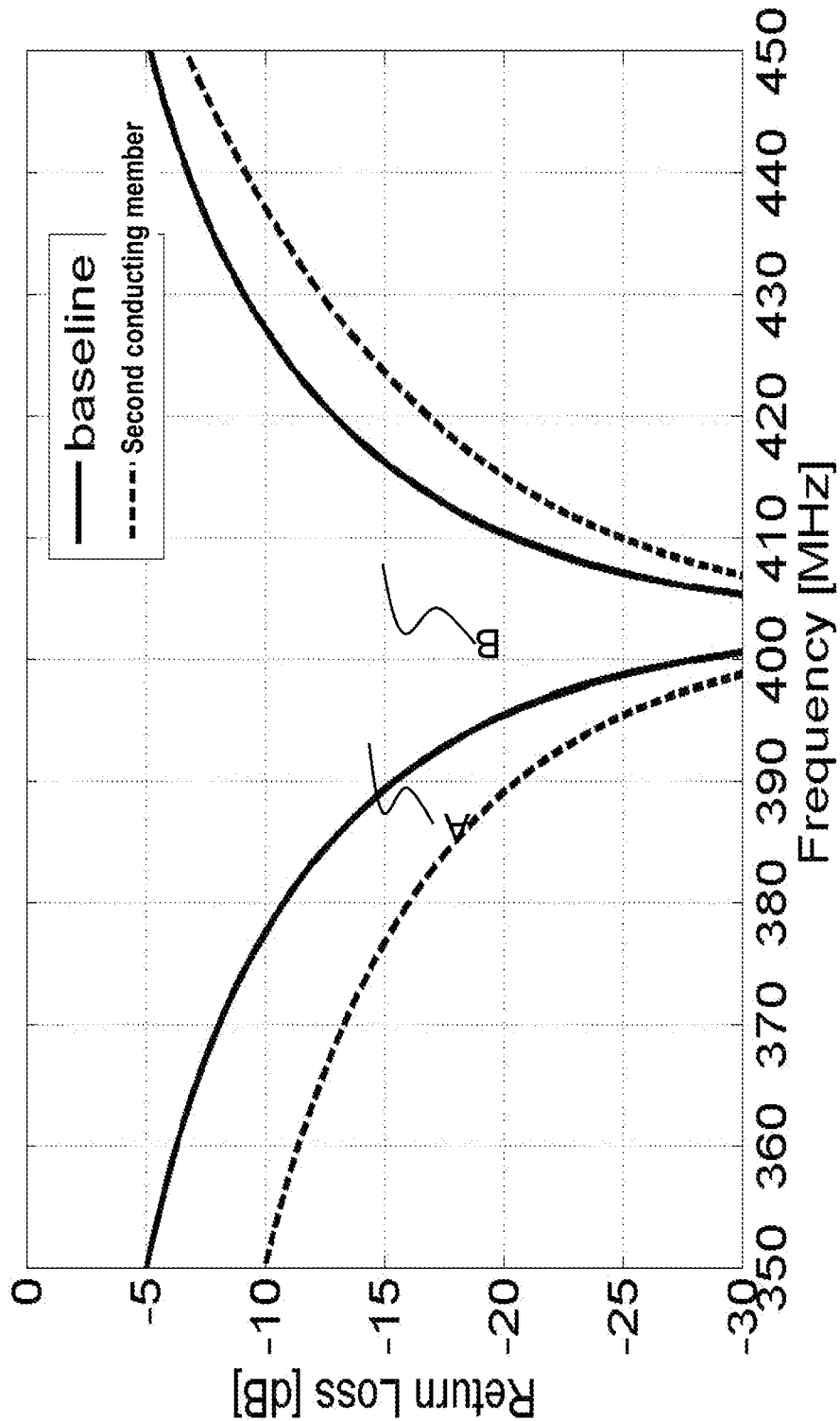
FIG. 1 is the result of an antenna simulation of an antenna without (curve A) and with (curve B) the second conducting members in the form of a full ring in an FFC torso simulator showing the return loss (in dB) versus the frequency (in MHz).

The plot of FIG. 1 shows that the addition of the ring increases the bandwidth of the antenna from 50 MHz to 87 MHz compared to a design without the second conducting member (curve A).

Figure 2:
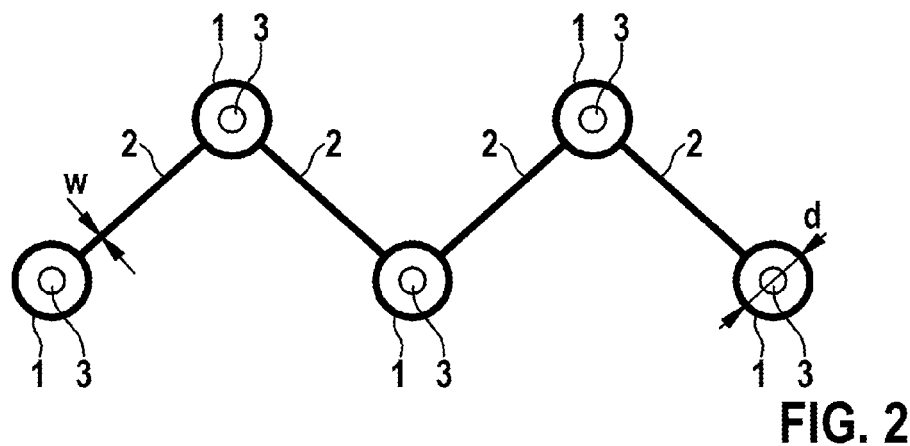
FIG. 2 is a first embodiment of an antenna according to the present invention in a top view.

FIG. 2 illustrates a first embodiment of an antenna according to the present invention. The antenna comprises electrically conducting rings 1 as second conducting members with through going openings 3 (i.e., holes) which are electrically connected by strut-like first conducting members in the form of rods 2. The rods 2 form a zig-zag structure, wherein the rings 1 are accommodated at the turning points of the structure. Adjacent rods 2 enclose an angle of approximately 120°. The width "w" of a rod 2 is about 0.8 mm, and the outer diameter d of a disc or the ring 1 is about 2 mm. Further, the diameter D of the opening 3 (see FIGS. 6-7 with regard to the opening 33) is about 0.8 mm. The material of the conducting rings 1 and the rods 2 is Titanium grade 4. The thickness of the conducting layer forming the rods 2 and the rings 1 is about 0.1 mm.

Figure 3:
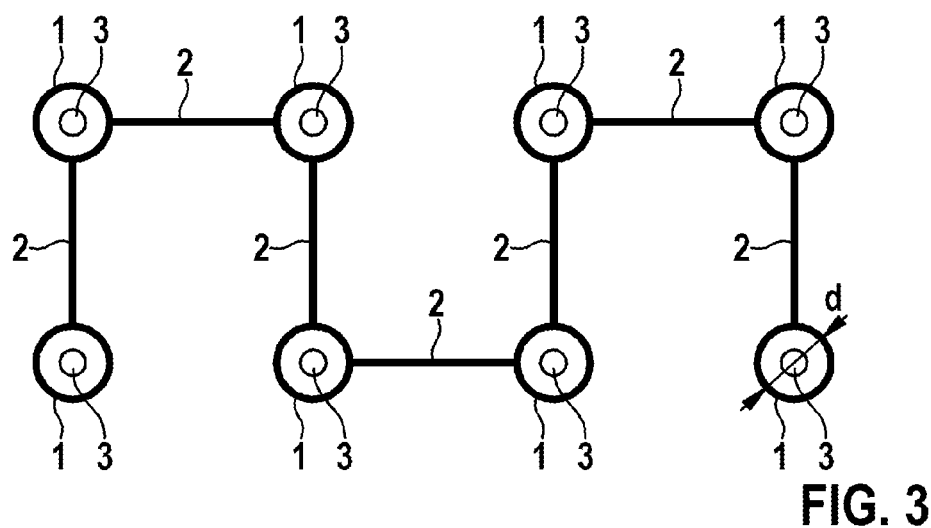
FIG. 3 is a second embodiment of an antenna according to the present invention in a top view.

FIG. 3 illustrates a similar structure, wherein the angle between two adjacent rods 2 is about 90°. Altogether, the structure of the antenna shown in FIG. 3 has the form of a square function design, wherein one conducting ring 1 is accommodated at each turning point between two adjacent rods 2.

Figure 4:
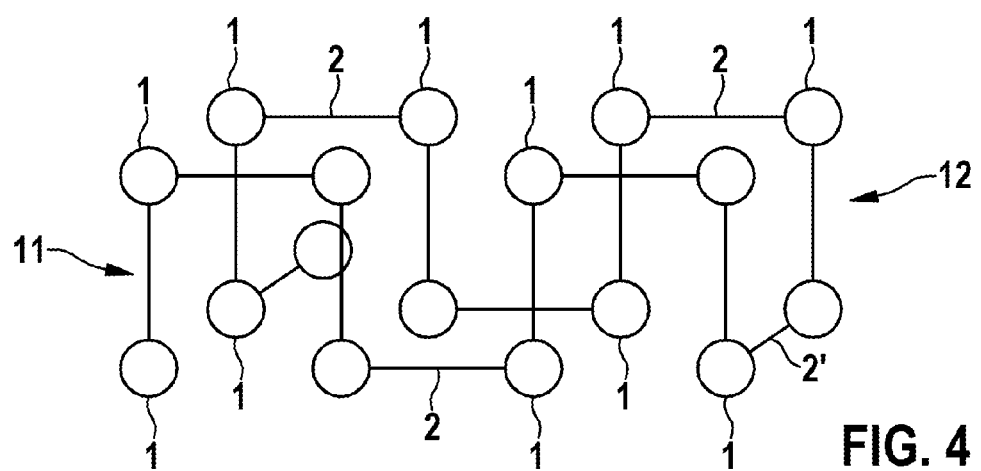
FIG. 4 is a third embodiment of an antenna according to the present invention in a perspective view.

FIG. 4 discloses a third embodiment of an antenna, as shown in FIG. 4, and is similar to the structure disclosed in FIG. 3, but the structure extends to two different planes of the device, namely, a first section 11 in a first plane or first layer, and a second section 12 in a second plane or second layer, which is parallel to the first plane. The first section 11 and the second section 12 are electrically connected by the strut (rod) 2' which runs perpendicular to the first section 11 and the second section 12. The embodiment disclosed in FIG. 4 has conducting members 1 in form of disks, i.e., it lacks of through going openings 3. In one or more embodiment not shown in FIG. 4, the conducting members can be shaped in any kind of three dimensional forms, like spheres, or ellipsoids, or the like. These three dimensional forms can comprise, or cannot comprise, through going openings 3. In other embodiments, these three dimensional forms can be solid, or hollow, or hollowed out. In addition, these hollow or hollowed out forms can have said through going openings 3.

Figure 5:
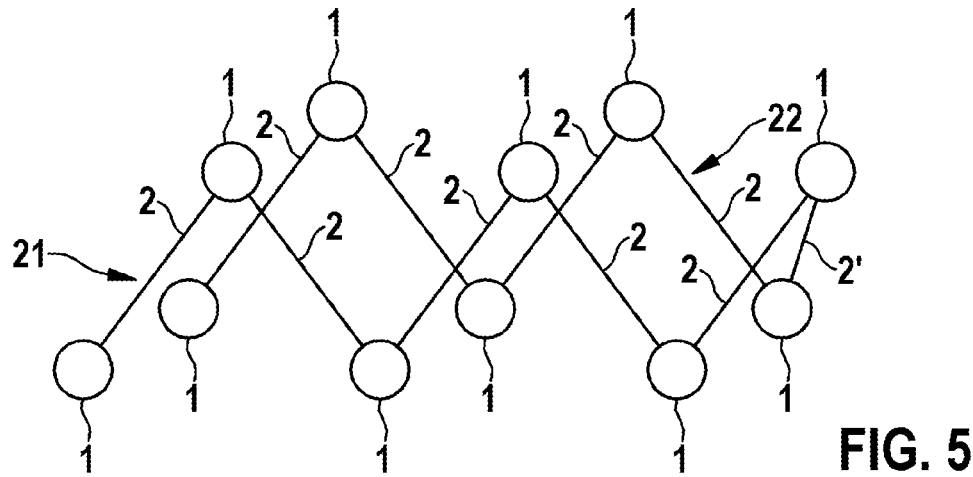
FIG. 5 is a fourth embodiment of an antenna according to the present invention in a perspective view.

In at least one further embodiment, FIG. 5 illustrates the structure of FIG. 2 in two parallel layers, wherein the first section 21 is accommodated in a first plane and the second section 22 in a second plane. The first section 21 and the second section 22 are electrically connected by the strut (rod) 2' running transversely to the first plane and the second plane.

Figure 6:
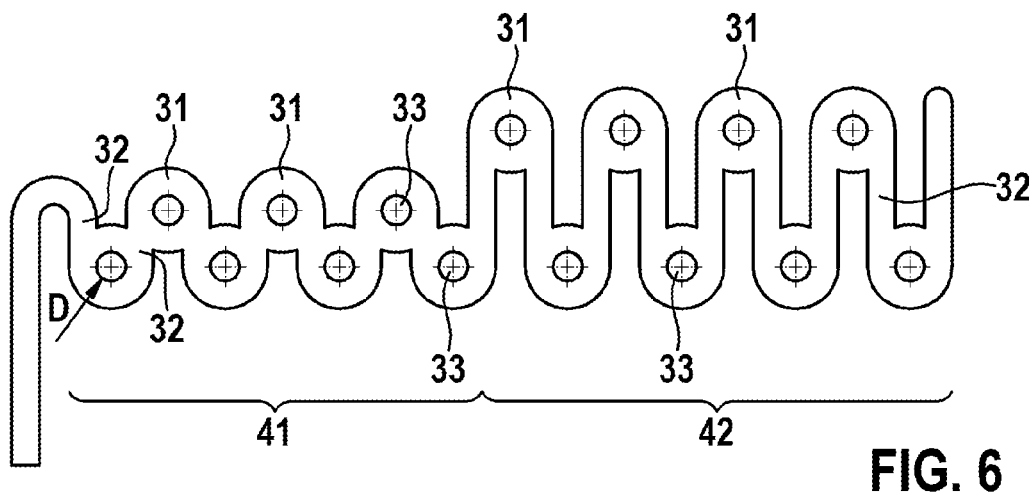
FIG. 6 is a fifth embodiment of an antenna according to the present invention in a top view.

FIG. 6 discloses at least one embodiment of an antenna, wherein each second conducting member in form of a ring 31 with a through-going opening 33 is connected by a first conducting member in the form of a rod 32 with the next, adjacent ring 31. The rods 32 run parallel to each other. Further, in one or more embodiments, the antenna, as shown in FIG. 6, comprises a first section 41 and a second section 42, wherein the rods 32 of the first section 41 are shorter than the rods 32 of the second section 42. Thereby, a dual-band antenna is realized wherein the first section 41 of the antenna is resonant at some frequency and the second resonance of the second section 41 of the antenna is slightly different but nearby, thus providing operation over a further enhanced bandwidth.

Figure 7:
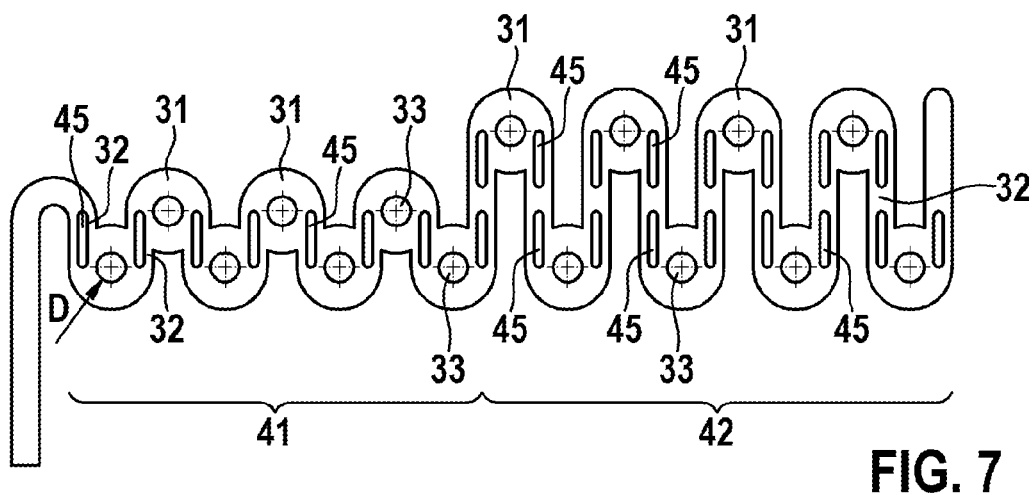
FIG. 7 is a sixth embodiment of an antenna according to the present invention in a top view.

FIG. 7 illustrates an embodiment of the antenna, which is similar to the antenna as shown in FIG. 6. Each rod of the first section 41 of the antenna comprises, in one or more embodiments, one or two through-going elongated holes, slits or slots 45. Each slot 45 extends to the adjacent ring 31. Each slot 45 runs parallel to the longitudinal axis of the respective rod 32. In some embodiments are two slots 45 in one rod 32, which are accommodated in series. The slots 45 have a width of about 0.3 mm. The purpose of the slots 45 is to increase the probability of electrons taking the long path around each ring 31. The slots 45 make it more difficult for electrons to travel the shorter route along the closer portions of any two consecutive rings 31. This increases the electrical length of the antenna over the design in FIG. 6 which does not have the slots.

Figure 8:
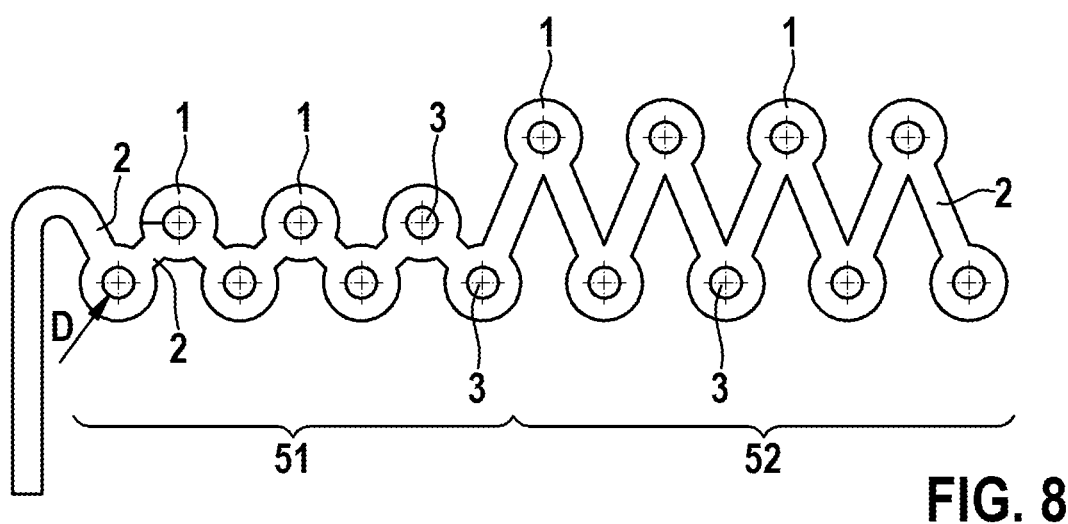
FIG. 8 is a seventh embodiment of an antenna according to the present invention in a top view.

FIG. 8 illustrates one or more embodiments, which are similar to the embodiment of FIG. 2. However, the antenna comprises a first section 51 and a second section 52, wherein each section 51, 52 has a different resonance frequency caused by rods 2 of different length analogous to the embodiment shown in FIGS. 6-7, thereby providing a higher bandwidth.

The dimensions of the antenna structure of the embodiments depicted in FIGS. 3-8 are the same as the dimensions explained in connection with the embodiment shown in FIG. 2.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

LIST OF REFERENCE NUMBERS 1, 31 ring
2, 2', 32 rod
3, 33 through going opening
11 first section of antenna in a first plane or layer
12 second section antenna in a second plane or layer
21 first section of antenna in a first plane or layer
22 second section of antenna in a second layer
41 first section of antenna
42 second section of antenna
45 slot
51 first section of antenna
52 second section of antenna
A curve of return loss versus frequency for a modeled antenna without second conducting member
B curve of return loss versus frequency for a modeled antenna with second conducting member
d outer diameter of ring 1
D diameter of through going opening 3, 33
w width of rod 2, 2', 32

We claim:
1. An antenna comprising:
at least two strut-like first conducting members, wherein the at least two strut-like first conducting members run parallel to each other, and wherein each adjacent pair of first conducting members is connected by a second conducting member, wherein the second conducting member has the basic form of an at least partial round plate.
2. The antenna according to claim 1, wherein the second conducting member has the basic form of a full circle, wherein an at least one through going opening has a round or polygonal cross section.
3. The antenna according to claim 1, wherein the second conducting member further comprises at least one through going opening, wherein the basic form fully encircles the opening.
4. The antenna according to claim 1, wherein each of the at least two first conducting members and/or the second conducting member comprise an elongated slot.
5. The antenna according to claim 4, wherein each of the at least two first conducting members and/or the second conducting member comprise an elongated slot, which is through going.
6. The antenna according to claim 1, wherein one first conducting member has the form of a rod or a helix.
7. The antenna according to claim 1, wherein the at least two first conducting members and the intermediate second conducting member are accommodated in same planes.
8. The antenna according to claim 1, wherein the at least two first conducting members and the intermediate second conducting member are accommodated in different planes.
9. The antenna according to claim 1, wherein a first section of the antenna comprising at least one second conducting member and a pair of first conducting members is accommodated in a first plane, and a second section of the antenna comprising at least one second conducting member and a pair of first conducting members is accommodated in a second plane different from the first plane.
10. The antenna according to claim 1, wherein a first section of the antenna comprising at least one second conducting member and a pair of first conducting members is accommodated in a first plane, and a second section of the antenna comprising at least one second conducting member and a pair of first conducting members is accommodated parallel to the first plane.
11. The antenna according to claim 1, wherein the antenna further comprises a first section with a first resonant frequency and at least one second section with a second resonant frequency.
12. An implantable medical device comprising:
an antenna according to claim 1, accommodated within a header of the implantable medical device.
13. An implantable medical device comprising:
an antenna according to claim 11, where the first conducting members and the second conducting members are parallel to a wall or a side of a header of the implantable medical device.

* * * * *